(12) United States Patent
Bamford et al.

(10) Patent No.: US 9,792,693 B2
(45) Date of Patent: Oct. 17, 2017

(54) SPECTRAL UNMIXING

(71) Applicant: Ventana Medical Systems, Inc., Tucson, AZ (US)

(72) Inventors: Pascal Bamford, San Diego, CA (US); Srinivas Chukka, San Jose, CA (US); Lou Dietz, Mountain View, CA (US); Ronald T. Kurnik, Foster City, CA (US); Bikash Sabata, Cupertino, CA (US); Anindya Sarkar, Milpitas, CA (US); Olcay Sertel, Sunnyvale, CA (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 0 days.

(21) Appl. No.: 14/776,501

(22) PCT Filed: Mar. 13, 2014

(86) PCT No.: PCT/EP2014/055028
§ 371 (c)(1),
(2) Date: Sep. 14, 2015

(87) PCT Pub. No.: WO2014/140219
PCT Pub. Date: Sep. 18, 2014

(65) Prior Publication Data
US 2016/0035100 A1 Feb. 4, 2016

Related U.S. Application Data

(60) Provisional application No. 61/798,886, filed on Mar. 15, 2013.

(51) Int. Cl.
*G06T 7/00* (2017.01)
*G01J 3/44* (2006.01)
(Continued)

(52) U.S. Cl.
CPC .......... *G06T 7/0081* (2013.01); *G01J 3/4406* (2013.01); *G01N 21/6458* (2013.01); *G06T 7/11* (2017.01);
(Continued)

(58) Field of Classification Search
None
See application file for complete search history.

(56) References Cited

U.S. PATENT DOCUMENTS 7,688,442 B2 3/2010 Wolleschensky et al.
8,290,236 B2 10/2012 Lett et al.
(Continued)

FOREIGN PATENT DOCUMENTS

WO 20040113987 A1 12/2004

OTHER PUBLICATIONS

Zimmermann, "Spectral Imaging and Linear Unmixing in Light Microscopy," Adv Biochem Engin/Biotechnol (2005) 95: 145-165.*
(Continued)

*Primary Examiner* — Matthew Bella
*Assistant Examiner* — Soo Shin

(57) ABSTRACT

Processing of images acquired via fluorescence microscopy by identifying broadband and other undesired signals from the component signals of a scanned image, and processing selected regions of the image that are known to contain signals of interest, thereby extracting or identifying desired signals while subtracting undesired signals. One or more broadband signals are recognized by their unique signature and ubiquitous dispersion through the image. Regions of the scanned image may be tagged as consisting of predominantly broadband signals and are ignored during a spectral unmixing process. The remaining regions of the image, or selected regions of the image known to contain desired signals, may be unmixed, and the plurality of reference
(Continued)

spectra subtracted from the components to extract or identify the target signals. The set of target signals may be refined by eliminating known or obvious sources of noise by, for instance, being compared to known or ideal sets of signals from similar materials.

30 Claims, 11 Drawing Sheets

(51) Int. Cl.
*G01N 21/64* (2006.01)
*G06T 7/11* (2017.01)

(52) U.S. Cl.
CPC ............... *G01N 2021/6421* (2013.01); *G06T 2207/10064* (2013.01)

(56) References Cited

U.S. PATENT DOCUMENTS

| | | | | |
|---|---|---|---|---|
| 2005/0136258 A1* | 6/2005 | Nie | ................. | A61K 47/48861 428/402 |
| 2008/0051665 A1* | 2/2008 | Xu | ..................... | A61B 5/0059 600/476 |
| 2008/0212866 A1 | 9/2008 | Lett et al. | | |
| 2008/0294032 A1* | 11/2008 | Levenson | ............ | A61B 5/0059 600/407 |
| 2013/0109019 A1* | 5/2013 | Murillo | ............ | A61K 47/48007 435/6.11 |
| 2014/0078286 A1* | 3/2014 | Bamford | .............. | G06K 9/0014 348/79 |

OTHER PUBLICATIONS

Van Benthem, M. and Keenan, M., "Fast algorithm for the solution of large-scale non-negativity-constrained least squares problems." Journal of Chemometrics vol. 18, No. 10, pp. 441-450, (2004).

Keshava, N., "A survey of spectral unmixing algorithms." Lincoln Laboratory Journal vol. 14, No. 1, pp. 55-78, (2003).

Pengo, T., et al., "Spectral unmixing of multiply stained fluorescence samples." Microscopy: Science, Technology, Applications and Education. Microscopy Book Series, No. 4, pp. 2079-2087, (2010).

Lawson, C. L., and Hanson, R. J. "Solving least squares problems." pp. 161, chap. 23, (1974).

* cited by examiner

SPECTRAL UNMIXING

CROSS REFERENCE TO RELATED APPLICATIONS

This application is a U.S. National Phase application of PCT/EP2014/055028, filed on Mar. 13, 2014, entitled "SPECTRAL UNMIXING", which claims the benefit under 35 U.S.C. §119(e) of and priority to U.S. Provisional Patent Application No. 61/798,886, filed Mar. 15, 2013, which is herein incorporated by reference in its entirety.

BACKGROUND OF THE SUBJECT DISCLOSURE

Field of the Subject Disclosure

The present subject disclosure relates to spectral unmixing in fluorescence microscopy. More particularly, the present subject disclosure relates to estimating reference spectra for predominantly broadband regions of an image and using the reference spectra to unmix desired regions of the image.

Background of the Subject Disclosure

In the analysis of biological specimens such as tissue sections, blood, cell cultures and the like, fluorescence microscopy is used to generate images of biological specimens which are stained with one or more fluorophores. Biological specimens, such as tissue sections from human subjects, can be treated with a stain containing an organic fluorophore conjugated to an antibody which binds to protein, protein fragments, or other targets in the specimen. For instance, the specimen may be stained with 4',6-diamidino-2-phenylindole (DAPI). The stained specimen is then illuminated with light and the stain fluoresces. A digital camera attached to a microscope is then used to capture an image of the specimen. The areas where the fluorophore/antibody combination became bound to the target of interest (e.g., proliferation protein produced by cancerous cells) appear as colored regions in the image of the specimen, with the color of the area dictated by the fluorescence spectrum of the fluorophore applied to the specimen. In addition to the visible spectrum, the fluorescence signal may be detected in the infra-red or ultra-violet regions, depending on emission spectrum of the particular fluorophore. A stain containing two or more fluorophores can also be applied to the specimen. These methods have a variety of uses, including diagnosis of disease, assessment of response to treatment, and development of new drugs to fight disease. Recently increased use of nano-crystalline luminescent semiconductor materials known as "quantum dots" as a stain material for biological staining and imaging applications poses several advantages over traditional organic fluorophores. These advantages include narrow emission band peaks, broad absorption spectra, intense signals, and strong resistance to bleaching or other degradation.

An observed signal is typically a mixture of multiple signals that are linearly mixed. The problem of unmixing them, i.e. going back to the original components from the observed signal, is solved by spectral unmixing the resulting image or portions thereof. This is a standard linear algebra problem that is properly applied to positive (or non-negative) signals, such as those emitted by fluorophores. Thus, a non-negative linear least squares method is typically used. For instance, in medical imaging, each location may include 16 signals, where the goal would be to isolate between 6-10 desired signals, or signals that are known to correspond to a quantum dot or other target signal. However, there is a mixture of signals at each point or pixel in the image. Therefore, for a 10,000×10,000 image with 16 channels, the unmixing process would be resource-intensive and cumbersome. Traditionally, one would unmix at each location or pixel using a linear equation solver. However, a complication arises when autofluorescence and DAPI are in the spectrum of detected signals. These are broadband signals, noisy, and hide the quantum dots. Autofluorescence and DAPI change from image to image, and from location to location, and this results in intensive computation and unclear results. This is further complicated by variety in sample types, such as tissues from various organs and organisms. Even known broadband signatures, when applied universally to specific samples, rest on an assumption that these reference spectra are fixed throughout the image, and thereby lead to imperfect results. DAPI, for instance, is only useful for staining nuclei and getting a context of the image. Also, DAPI is a broadband signal, that overwhelms other signals, and occurs in large regions. The same applies to red blood cells (RBCs) and lipofuscin, which respectively have highly broadband signals (RBC), and autofluorescence (lipofuscin). These signals are largely unnecessary from a diagnostic perspective, and it is desired that they are removed.

SUMMARY OF THE SUBJECT DISCLOSURE

The subject disclosure processes images acquired via fluorescence microscopy by identifying broadband signals such as autofluorescence, etc. from the component signals of a scanned image, generating reference signals from the broadband signals, and using the reference signals to unmix selected regions of the image that are known to contain signals of interest, or "target signals." A received image may comprise a mixture of several fluorescent channels including one or more target signals, such as quantum dots, mixed with one or more broadband signals. The one or more broadband signals are recognized by their unique signature and ubiquitous dispersion through the image. The ubiquitously-dispersed broadband signals are recognized based on a comparison of their signature with a known signature from a known broadband signal. One or more reference signals (or reference spectra) may be generated based on the broadband signals measured in the image and based in part on the comparison with the known signal. Selected "target regions" of the image that are known to contain target signals may be unmixed using the reference signals, and target signals extracted from the results. A linear spectral unmixing process, such as a non-negative linear least-squares method, may be utilized to separate the component fluorescent channels in the target regions. Additional regions consisting predominantly of broadband signals may be identified based on the reference signals, and may be ignored by or tagged as being exempt from the spectral unmixing process. A resultant set of target signals may be refined by eliminating known or obvious sources of noise by, for instance, being compared to known or ideal sets of signals from similar materials. The system therefore enables generation of an image substantially consisting of desired target signals without any broadband noise or undesired fluorescent artifacts, enabling efficient image analysis, identification of structures, accurate diagnoses, etc.

In one exemplary embodiment, the present subject disclosure is a non-transitory computer-readable medium for storing computer-executable instructions that are executed by a processor to perform operations comprising receiving an image comprising a mixture of signals, the mixture of signals further comprising a measured broadband signal and a target signal, detecting a location of a first region of the image, the first region predominantly comprising the measured broadband signal, the detecting being based on a comparison of the measured broadband signal with a known broadband signal, estimating a reference signal for the image based on the measured broadband signal, and utilizing the reference signal to spectrally unmix the mixture.

In another exemplary embodiment, the present subject disclosure is a non-transitory computer-readable medium for storing computer-executable instructions that are executed by a processor to perform operations comprising detecting a predominantly broadband region of an image, the image comprising a mixture of broadband signals and target signals, estimating a reference signal from the predominantly broadband region, and unmixing the mixture using the reference signal to extract the target signal.

In yet another exemplary embodiment, the present subject disclosure is a system for diagnosis of a tissue specimen, the system comprising a computer including a processor and a memory, a reference spectra determination module on the memory for detecting a location of a first region of an image, the image comprising a mixture of a measured broadband signal and a target signal, the first region predominantly comprising the measured broadband signal, the detecting being based on a comparison of the measured broadband signal with a known broadband signal, and estimating a reference signal for the image based on the measured broadband signal, and an unmixing module on the memory for applying a matrix comprising the reference signal to the mixture; and unmixing the mixture using the matrix to derive the target signal.

In yet another exemplary embodiment, the present subject disclosure is a method for spectral unmixing comprising scanning a slide holding a sample of a stained material using a fluorescent microscope to generate a scanned image, wherein the material is stained by means of application of a stain containing one or more different fluorophores, and wherein the scanned image comprises a mixture of signals, the mixture of signals further comprising a measured broadband signal and a target signal, detecting a location of a first region of the image, the first region predominantly comprising the measured broadband signal, the detecting being based on a comparison of the measured broadband signal with a known broadband signal, estimating a reference signal for the image based on the measured broadband signal, and utilizing the reference signal to spectrally unmix the mixture.

DETAILED DESCRIPTION OF THE SUBJECT DISCLOSURE

Figure 1:
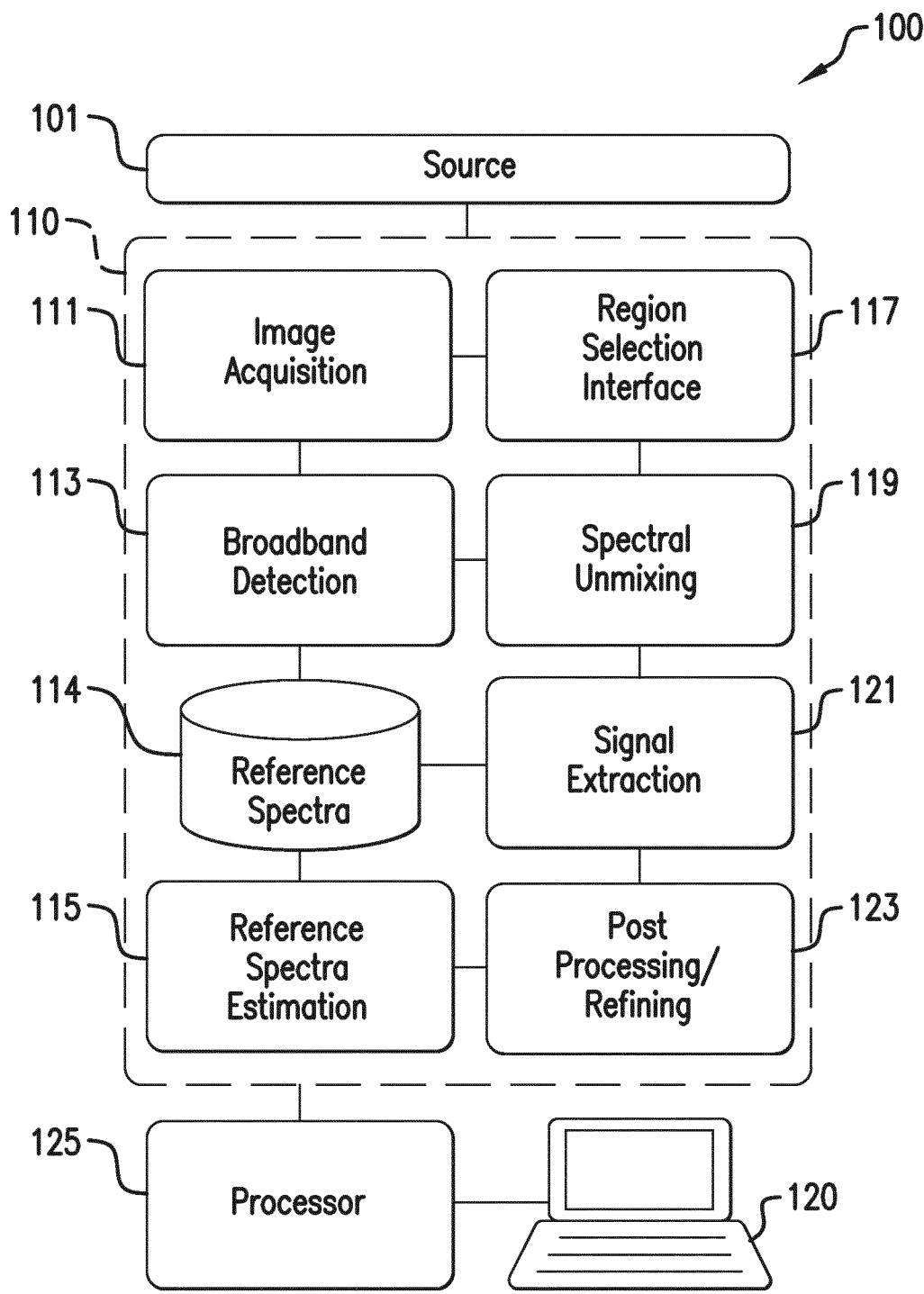
FIG. 1 shows a system for enhanced spectral unmixing, according to an exemplary embodiment of the present subject disclosure.

The subject disclosure processes scanned fluorescent images to separate or "unmix" component signals of the scanned image and extract or identify desired signals while ignoring undesired signals. For example, the subject disclosure processes captured fluorescent channel data to separate or "unmix" component signals and extract or identify desired signals while ignoring undesired broadband component signals. Although the spectral unmixing method described in this application is applied to two dimensional image data (data captured on fluorescent microscope or whole slide scanner), it is also applicable to one-dimensional data (e.g., data obtained via mass spectroscopy) and three-dimensional data (e.g., data captured via volume scanning).

In accordance with the present invention, a slide holding a sample material may be scanned using a fluorescent microscope to generate a scanned image. The image is stored on a computer-readable medium, and contains a mixture of several fluorescent channels, including one or more desired or target signals mixed with one or more broadband signals. The one or more broadband signals are recognized by their unique signature and ubiquitous dispersion through the image. The ubiquitously-dispersed broadband signals are recognized based on a comparison of their signature with a known signature from a known broadband signal. Upon determining a component signal having a broadband profile or signature, the signature may be compared to a known broadband signal specific to the sample material being analyzed. For instance, a system for anatomical or clinical pathology may compare a scanned image of a tissue sample with a calibration slide holding a similar tissue sample. A rough match between the broadband signals of each sample may trigger a positive identification of the broadband signal in the scanned image.

One or more reference signals (or reference spectra) may be generated based on the broadband signals measured in the image and based in part on the comparison with the known signal. The reference spectra may be stored as an array or matrix, and subsequently applied to the entire image, or to selected regions of the image that are known or suspected to include target signals. The selected target regions of the image may be unmixed using the reference spectra, and target signals extracted from the results. A linear spectral unmixing process, such as a non-negative linear least-squares method shown herein, may be utilized to separate the component fluorescent channels in the target regions. The regions consisting predominantly of broadband signals may be ignored by or tagged as being exempt from a spectral unmixing process. Such recognition of predominantly noisy regions of the image enables selective spectral unmixing of only the remaining regions, or regions identified as being of interest to a user.

For instance, a region selection interface may be employed to select or "tag" regions of the scanned image consisting of predominantly broadband signals. The tagged regions may be ignored, or exempt from being processed by a spectral unmixing algorithm, enabling speedier extraction of desired or target signals from the mixture of component signals comprising the image. The set of target signals may be reconstructed to generate an image that is free from any noisy or unwanted spectra, and consequently fit for analysis. The set of target signals may be further refined by eliminating known or obvious sources of noise by, for instance, being compared to known or ideal sets of signals from similar materials. Other refinement processes include adjusting a minimum or a maximum of intensities to highlight a specific range and eliminating signals outside the range, adjusting a contrast to see a more dynamic range, and other imaging operations.

The disclosed systems and methods therefore enable generation of an image substantially consisting of desired or precise signals without any broadband noise or undesired fluorescent artifacts. For instance, autofluorescence, DAPI, and other undesired signatures may be identified for a scanned image of a specific tissue sample, and removed from the component signals of a region of the image that is known to contain biologically relevant information. Moreover, once a broadband signature is determined for a particular slide or set of slides, predominantly broadband regions need not be unmixed, resulting in a less intensive unmixing process. The disclosed features therefore enable efficient image analysis, identification of structures, accurate diagnoses, etc.

For the following description, it can be assumed that most correspondingly labeled structures across the figures (e.g., 132 and 232, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIG. 1 shows a system 100 for spectral unmixing, according to an exemplary embodiment of the present subject disclosure. System 100 comprises a source 101 for generating a fluorescent image. For instance, source 101 may be a spectral camera, a scanner, or a fluorescence microscope associated with or including a scanner or spectral camera that is used for imaging a slide containing a sample of a material stained with a fluorescent stain. Source 101 is in communication with a memory 110, which includes a plurality of processing modules or logical instructions that are executed by processor 125 coupled to computer 120. For instance, a sample, such as a biological specimen, may be mounted on a slide or other substrate or device for purposes of imaging by a camera or microscope coupled to memory 110, with analysis of images of the sample being performed by processor 125 executing one or more of the plurality of modules stored on memory 110 in accordance with the present disclosure. The analysis may be for purposes of identification and study of the sample. For instance, a biological or pathological system may study the sample for presence of proteins, protein fragments or other markers indicative of cancer or other disease, or for other purposes such as genomic DNA detection, messenger RNA detection, protein detection, detection of viruses, detection of genes, or other.

The sample may be stained by means of application of a stain containing one or more different fluorophore(s). The number N of fluorophores that are applied to the sample can vary, but will typically be between 2 and 10. The fluorophores may comprise one or more nano-crystalline semiconductor fluorophores (i.e., quantum dots), each producing a peak luminescent response in a different range of wavelengths. Quantum dots are well known, and may be commercially available from Invitrogen Corp., Evident Technologies, and others. For example, the sample may be treated with several different quantum dots, for example quantum dots which produce a peak luminescent response at 565, 585, 605, and 655 nm. One or more of the fluorophores applied to the sample may be organic fluorophores 14 (e.g., DAPI, Texas Red), which are well known in the art, and are described in at least commonly-owned and assigned U.S. Pat. No. 8,290,236, the contents of which are incorporated by reference herein in their entirety.

Thus, system 100 can be used with a sample that is stained with just quantum dots, with quantum dots in combination with conventional organic fluorophores, or just conventional organic fluorophores. Moreover, a typical sample is processed in an automated staining/assay platform that applies a stain containing quantum dots and/or organic fluorophores to the sample. There are a variety of commercial products on the market suitable for use as the staining/assay platform, one example being the Discovery™ product of the assignee Ventana Medical Systems, Inc. After preliminary tissue processing and staining, the sample is supplied to a camera system including a spectrum source, for example, a light source for illuminating the sample at wavelengths intended to produce a luminescent response from the fluorophores applied to the specimen. In the case of quantum dots, the light source may be a broad spectrum light source. Alternatively, the light source may comprise a narrow band light source such as a laser. The camera platform may also include a microscope having one or more objective lenses and a digital imager, as well as a set of spectral filters.

Other techniques for capturing images at different wavelengths may be used. Camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure.

The image may be supplied to computer-readable medium 110, either via a cable connection between the microscope 101 and computer 120, via a computer network, or using any other medium that is commonly used to transfer digital information between computers. The image may also be supplied over the network to a network server or database for storage and later retrieval by computer 120. Besides processor 125 and memory 110, computer 120 also includes user input and output devices such as a keyboard, mouse, stylus, and a display/touchscreen. As will be explained in the following discussion, processor 125 executes logical instructions stored on memory 110, performing analysis of the image, morphological processing of the image or image data derived from such images, quantitative analysis, and display of quantitative/graphical results to a user operating computer 120.

For instance, as described above, a slide holding a sample material is scanned at source 101 to generate a scanned image comprising a mixture of several fluorescent channels including one or more desired or target signals mixed with one or more broadband signals. The image is received by image acquisition module 111. The image may not be generated as yet, and simply the mixture of signals may be acquired by image acquisition module 111 and subsequently processed by broadband detection module 113. One or more broadband signals within the mixture of signals may be recognized by their unique signature and ubiquitous dispersion through the image. Certain regions of the image may be determined to contain predominantly, or only, a broadband signal, such as autofluorescence, etc. The broadband profile of these signals along with their ubiquitous dispersion throughout the image support an assumption that these regions highly likely do not contain any useful information, such as peaks from desired signals.

Moreover, upon determining a component signal having a broadband signature, the component signal may be compared with known broadband signatures specific to the sample material being analyzed. For instance, a system for anatomical or clinical pathology may compare a scanned slide of a tissue sample with an image of a calibration slide containing similar tissue samples having known broadband signatures, to identify the broadband signals in the scanned image. The known broadband signatures may be stored in reference spectra database 114. For instance, a human tissue specimen may be known to include a broadband signature corresponding to red blood cells (RBCs). Reference spectra database 114 may include the known signature for the RBCs, and biological information, such as DAPI signatures corresponding to the tissue type, autofluorescence, etc. The known broadband signature may be compared with regions of the image to recognize predominantly broadband signals within said regions. For instance, a region of the image that is known to predominantly contain broadband signatures may be compared with corresponding a priori information about known sample types and, based on a similar underlying shape or signature, these regions are assumed to correspond to the known broadband signatures.

Further, a plurality of reference signals, or reference spectra, may be estimated based upon the comparison of the signatures of the measured broadband signals and the known broadband signals. Reference spectra estimation module 115 may perform operations on the measured broadband signals, based on known broadband signals from reference spectra database 114, to generate a plurality of reference spectra. These reference spectra may be used to further identify additional regions of the image that predominantly comprise or consist of broadband signals. These regions may be selected or "tagged" as having no useful components or target signals. The tagging may be enabled by a region selection interface module 117 enabling a user or the system to select or "tag" regions of the scanned image consisting of predominantly broadband signals. The tagged regions may be ignored, or exempt from being processed by a spectral unmixing module 119, enabling speedier extraction of desired or target signals from the mixture of component signals comprising the image. As the broadband signals are typically constant or slow-varying through a single image, the predominantly noisy regions may be automatically tagged by region selection interface 117, with a user being provided an option to untag certain regions of interest. Further, a user may preselect or tag regions of the image that are known to contain additional or useful signals such as quantum dots, etc., as regions designated to be processed by the spectral unmixing module 119. This tagging of regions as wanted or unwanted identifies a plurality of regions of the image that consist predominantly of broadband signals and therefore may not be useful, or may be considered as noisy. Such recognition of predominantly noisy regions of the image enables selective spectral unmixing of only the remaining regions, or regions identified as being of interest to a user.

Subsequent to region selection, spectral unmixing module 119 may be invoked to unmix the component signals of the desired regions of the image. The reference spectra estimated by reference spectra estimation module 115 may be stored within an array or a matrix comprising a plurality of known signals, including narrowband signals corresponding to target signals in the image. The matrix may be applied to unmix the remaining regions of the image to enable extraction of one or more target signals, as shown in more detail below. For example, a linear spectral unmixing process may be utilized to separate the component fluorescent channels in the scanned image using the estimated reference spectra, and a signal extraction module 121 executed to retrieve a set of one or more target signals. A spectral signature of a single pixel in the multi-channel image is obtained as a linear combination of the spectral signatures of all the different fluorophores, each signature being weighted by the corresponding weight of each fluorophore at that pixel. In a multi-channel image, there may not be any access to the individual weight for each fluorophore's combination; however, the spectral signature of each pixel may be retrieved. The mathematical process by which the weight of each fluorophore is computed at every image pixel, given the spectral signature at each pixel, is known as spectral unmixing. The set of spectral or target signals retrieved may be reconstructed to generate an image that is free from any noisy or unwanted spectra, and consequently fit for analysis.

The set of target signals may further be refined by a postprocessing/refining module 123 that eliminates known or obvious sources of noise by, for instance, being compared to known or ideal sets of signals from similar materials. For instance, it may be known that two specific quantum dots are unable to coexist in a certain sample material. This "impossibility" may be recognized by post-processing module 123, and accounted for by removing the offending signal, leaving behind a refined set of target signals. The known impossibility may be retrieved from reference spectra database 114, or any other data store in communication with the system, or a skilled operator of the system, such as a pathologist or knowledgeable technician. Further, other refinement operations such as adjusting a minimum or a maximum of intensities may be applied to the target signals to highlight a specific range and eliminate signals outside the range. An image resulting from the set of target signals may be adjusted for contrast to see a more dynamic range of target signals. For instance, data obtained after spectral unmixing may be of insufficient resolution in terms of its dynamic range, and therefore a brightness or contrast adjustment (which artificially increases the dynamic range of the image content for the unmixed channels) may make it visually easier to perceive how strong the unmixed channels are at different pixels in the image. Such adjustments enable studying an output from an unmixed channel and improve image understanding. Other imaging operations may be performed, with any resultant image, as well as interfaces for executing and manipulating the modules stored in memory 110, being depicted on a display of computer 120.

As described above, the modules include logic that is executed by processor 125. "Logic", as used herein and throughout this disclosure, refers to any information having the form of instruction signals and/or data that may be applied to affect the operation of a processor. Software is one example of such logic. Examples of processors are computer processors (processing units), microprocessors, digital signal processors, controllers and microcontrollers, etc. Logic may be formed from signals stored on a computer-readable medium such as memory 110, which includes including random access memory (RAM), read-only memories (ROM), erasable/electrically erasable programmable read-only memories (EPROMS/EEPROMS), flash memories, etc. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network.

Figure 2:
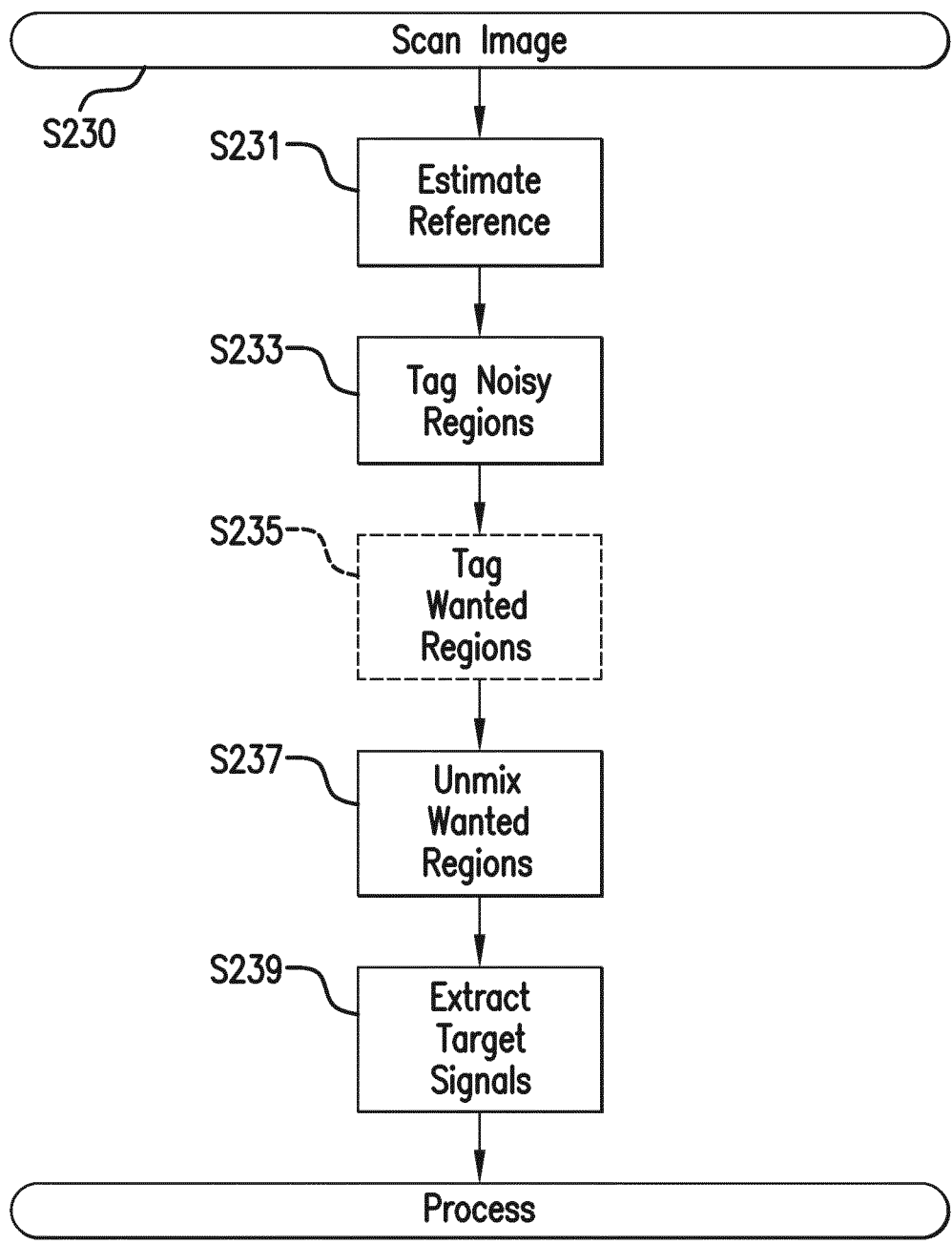
FIG. 2 shows a method for enhanced spectral unmixing, according to an exemplary embodiment of the present subject disclosure.

FIG. 2 shows a method for spectral unmixing, according to an exemplary embodiment of the present subject disclosure. The method of FIG. 2 may be performed by a computer executing modules similar to those depicted in FIG. 1. The method begins with an image of a sample that has been received from a source such as a fluorescence microscope associated with or including a scanner or spectral camera (S230), or any source that can capture image content at a range of frequencies, enabling hyperspectral or fluorescence imaging wherein the image energy is captured at multiple frequencies. The sample may be stained by means of application of a stain containing one or more different fluorophores, illuminated by, for example, a light source, and an image captured by a camera, as described above. The image is supplied to a computer that executes logical instructions stored on a memory for performing the operations described in the exemplary method. For instance, reference spectra for the broadband signals in the image, such as autofluorescence, are estimated (S231). This step includes recognizing one or more broadband signals based on their unique signature and ubiquitous dispersion through the image. Certain regions of the image may be determined to contain predominantly, or only, a broadband signal, such as autofluorescence, etc. The broadband profile of these signals along with their ubiquitous dispersion throughout the image support an assumption that these regions highly likely do not contain any useful information, such as peaks from target signals. Component signals having a broadband profile may be compared with known broadband signatures specific to the sample material being analyzed. For instance, a system for anatomical or clinical pathology may compare a scanned image of a tissue sample with a calibration slide of a similar tissue sample having a known broadband signature to identify the measured broadband signals in the scanned image. This determination may further be enabled by referring to a reference spectra database storing a plurality of reference spectra corresponding to known broadband signatures for the type of sample being analyzed. Reference spectra may then be estimated from the measured broadband signals, and stored in a matrix.

A plurality of regions that predominantly comprise or consist of broadband signals are identified. The reference spectra determined from the measured broadband signal may be used to identify these regions. These regions may be tagged as being ignored or undesired (S233). Tagging these regions as being exempt from being unmixed enables speedier extraction of desired or target signals from the mixture of component signals comprising the image. Since the broadband signals are typically constant or slow-varying through a single image, the predominantly noisy regions may be automatically tagged, or selected by a user. Further, regions of the image that are known to contain additional or useful signals such as quantum dots, etc., may optionally be tagged as designated to be processed by spectral unmixing (S235). This tagging of regions as wanted or unwanted identifies a plurality of regions of the image that consist predominantly of broadband signals and therefore may not be useful, or may be considered as noisy. Such recognition of predominantly noisy regions of the image enables selective spectral unmixing of only the remaining regions, or regions identified as being of interest to a user. A user interface for selecting regions of an image is further described with reference to FIG. 4.

Subsequent to region selection, regions of the image indicated to be of interest may be unmixed into their component signals by a spectral unmixing process (S237). For example, a linear spectral unmixing process using a least squares method may be utilized to separate the component fluorescent channels in the scanned image. The spectral unmixing process applies a matrix containing a plurality of reference signals, or reference spectra determined in step S231, to the measured mixture of signals, resulting in a plurality of unmixed component signals of the image. For instance, a matrix populated with reference spectra and a plurality of narrowband signals corresponding to the target signals may be applied to the mixture of signals, resulting in a set of component signals. The resultant set of component signals includes the broadband signals and the target signals, and the target signals may be extracted (S239). The set of desired signals may be reconstructed to generate an image that is free from any noisy or unwanted spectra, and consequently fit for analysis. Other processes may be performed on the set of desired signals, such as postprocessing/refining, etc., as described herein.

An example process for mixing and unmixing may be as follows. Let $Y=A*X$, where Y is a M×N matrix, A is a M×P matrix, and X is a P×N matrix, where a scanned image comprises M pixels, the spectral signature is a N-dimensional vector as it is measured over N frequency bands, and there are P fluorophores which contribute to the mixing process. Since the frequencies are physical in nature, a non-negative mixing model is assumed, with each element in A assumed to be non-negative. Considering a single pixel (the $i^{th}$ pixel), the linear mixing process is as follows:

$y_i = \Sigma a_{ij}$, where $1<=j<=P$ (number of fluorophores), $y_i$ is the spectral signature for the $i^{th}$ pixel and is a N-dimensional vector, $x_j$ is the spectral signature for the $j^{th}$ fluorophore and is a N-dimensional vector, and $a_{ij}$ is the linear combination factor for the $j^{th}$ fluorophore to the $i^{th}$ pixel to result in constructing the spectral signature for the $i^{th}$ pixel, $y_i$; since it is a physical process, $a_{ij} >= 0$ is assumed.

The unmixing process is as follows. If it is not assumed that the mixing terms $a_{ij}$ to be non-negative, the linear least squares solution to estimating A, where Y=AX is assumed is $A'=Y^{\dagger}X$, where $Y^{554}$ is the pseudo-inverse of Y. However, this solution does not ensure that each term in the estimated matrix A' is non-negative. Therefore, a non-negative linear least squares method is invoked. For the $i^{th}$ pixel, where $y_i = \Sigma a_{ij}$, assume that the estimated A terms are $\{a'_{ij}\}$. Then $\|y_i - \{\Sigma_{j=1, j=P} a'_{ij} x_j\}\|_2$, which is the $L_2$ norm distance between the $i^{th}$ spectral signature $y_i$, and the reconstructed spectral signature using the estimated A terms $\{\Sigma_{j=1, j=P} a'_{ij} x_j\}$, is considered and the best solution is the set of a' terms, $\{a'_{ij}\}_{j=1, j=P}$ which minimizes the norm $\|y_i - \{\Sigma_{j=1, j=P} a'_{ij} x_j\}\|_2$.

The solution mode for obtaining the a' terms is as follows: at first, unconstrained least squares is performed to minimize $\|y_i - \{\Sigma_{j=1, j=P} a'_{ij} x_j\}\|_2$ and in the solution space, it is observed which terms in a' are non-negative and which terms are negative. Then, in the solution space, a' terms (the dimensions which are non-negative are maintained while the dimensions which are not non-negative are reduced to zero) are found so as to minimize the $L_2$ norm. For each case, a Lagrange multiplier based formulation is used so as to preserve the correct indices (terms in where $1<=j<=P$, are considered and in the Lagrange multiplier format, the corresponding multipliers are set to −infinity for negative terms). The solution process in the non-negative linear least squares solver is an iterative process. In each iteration, consider the dimensions (out of P terms) in which are non-negative and make the other dimensions zero; and the intermediate solution is obtained using this non-negative set. In each set, the intermediate solution is used to decide on the perturbation to be applied to the current solution vector so as to make the solution vector non-negative. More details about the non-negative linear least squares solution process may be found in Lawson, C. L. and R. J. Hanson, *Solving Least Squares Problems*, Prentice-Hall, 1974, Chapter 23, p. 161.

Figure 3:
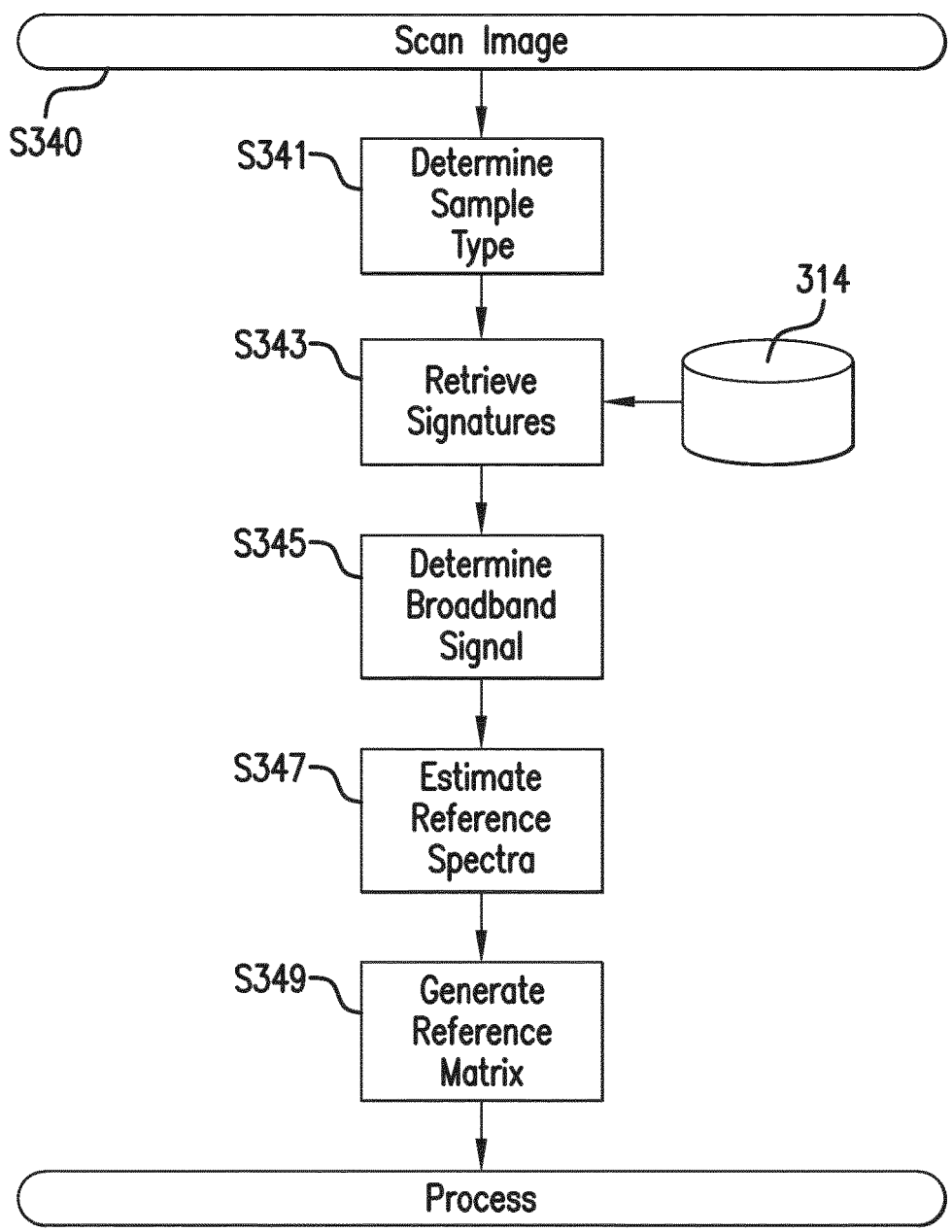
FIG. 3 shows a method for estimating reference spectra, according to an exemplary embodiment of the present subject disclosure.

FIG. 3 shows a method for estimating reference spectra, according to an exemplary embodiment of the present subject disclosure. The method of FIG. 3 may be performed by a computer executing modules similar to those depicted in FIG. 1. The method begins with an image of a sample that has been provided by a source, such as a fluorescence microscope (S340). The sample may be stained by means of application of a stain containing one or more different fluorophores, illuminated by a light source, and an image captured by a camera, as described above. The image is supplied to a computer that executes logical instructions stored on a memory for performing the operations described in the exemplary method. For instance, a type of sample may be determined (S341). This may occur by reviewing a tag or metadata associated with the image, input by a user, etc. The type of sample enables a database lookup to retrieve known broadband signatures for the particular sample type (S343). Reference spectra database 314 may store a plurality of known broadband signatures corresponding to tissue types similar to the type of sample being analyzed as identified in step S341. For instance, a system for anatomical or clinical pathology may compare a scanned image of a tissue sample with known broadband signatures for similar tissue samples to identify broadband signals in the scanned image.

Thereafter, measured component signals of the image having a broadband profile may be determined based on a comparison with the known broadband or narrowband signatures specific to, for example, the sample material being analyzed (S345). For instance, if a prostate tissue is being analyzed for a given range of frequencies, then the known broadband or narrowband signals for the various fluorophores may be collected from existing prostate tissue samples. For other tissue samples, such as breast or colon, it is possible that the DAPI spectrum may differ a bit and hence, for reliable unmixing, the known broadband spectra may be extracted from the "correct" samples (prostate tissue, in the present example). Further, narrowband spectra (such as quantum dots) have negligible variation in the reference spectra and, hence, it matters even less if the known signature is extracted from some other samples. In other words, a quantum dot spectra from a colon/breast will be similar to quantum dot spectra from a prostate.

A plurality of reference signals are then estimated from the measured broadband signals in the image (S347). This process is similar to the generation of reference spectra for calibration slides. For instance, a broadband signature of a plurality of pixels within a predominantly broadband region of the image may be averaged to determine a reference signal for the image. This process may be repeated for a plurality of broadband signals, such as autofluorescence for a particular tissue type. Such broadband signals may be substantially uniform, or slow-varying, throughout a particular slide, may be recognized based on their unique signature, as compared with the retrieved signatures in step S343, and ubiquitous dispersion through the image, and used to estimate the reference spectra. The estimated reference spectra may be used to populate a reference matrix comprising scaled versions of the estimated reference spectra and a plurality of signatures for target signals (S349).

This reference matrix may be used to unmix the observed mixture of signals using a non-negative linear least squares method, to arrive at a plurality of unmix component signals of the image.

For instance, let Y be an observed signal, consisting of 16 channels of fluorescence. Reference matrix X includes a plurality of reference spectra for up to six known signatures. Applying reference matrix X to the observed signals Y and using a non-negative least squares based minimizer framework yields desired results A (A={$a_j$} where $a_j$ denotes the contribution of the $j^{th}$ fluorophore to this current pixel, $1<=j<=6$ when 6 fluorophores are considered for unmixing). In other words, Y=AX, where Y can be thought of as a 1×16 matrix (the observation vector at this current pixel is obtained for 16 frequency bands yielding a 16-dimensional spectrum), and reference spectra matrix X is may be, for example, a 6×16 matrix, where each row may be, for example, 1×16, and corresponds to a reference spectrum of a certain fluorophore.

Figure 4:
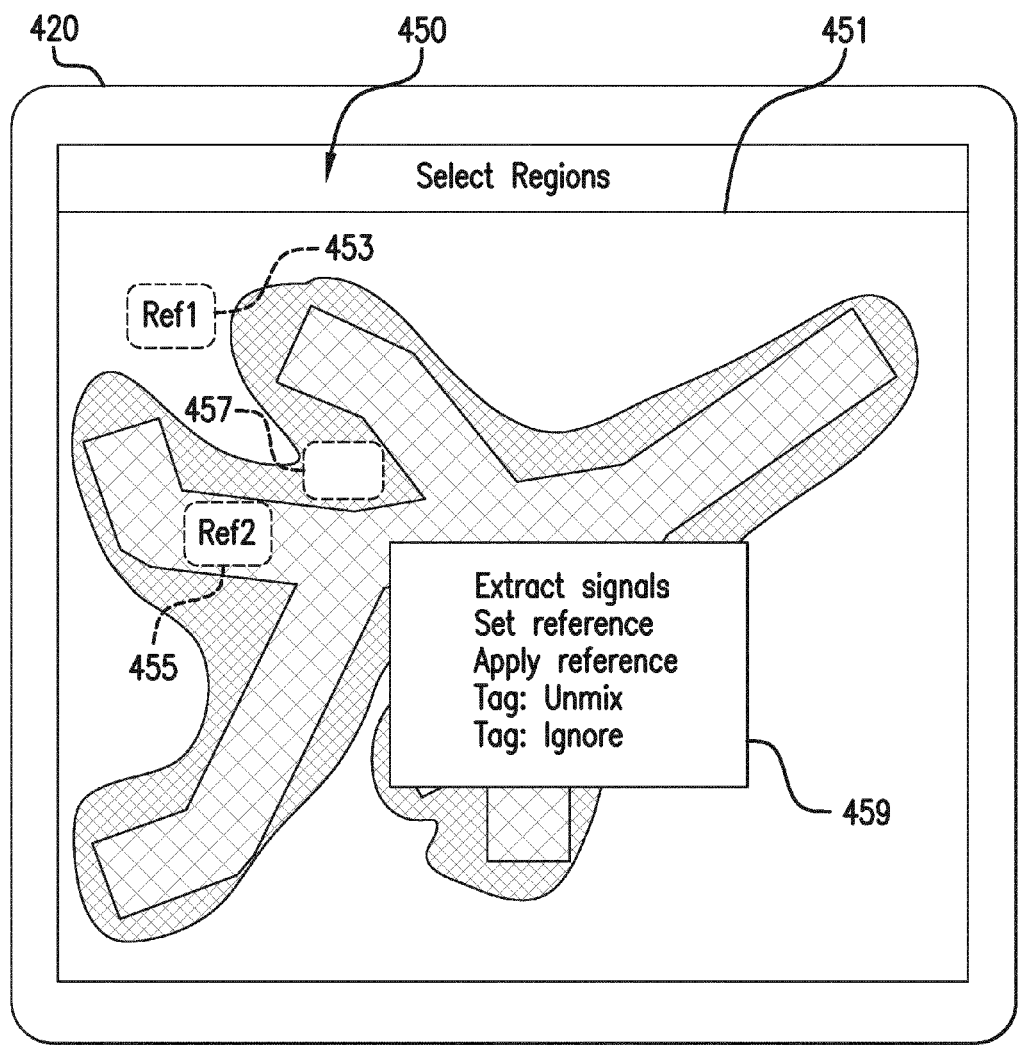
FIG. 4 shows a user interface for tagging regions of a scanned image, according to an exemplary embodiment of the present subject disclosure

FIG. 4 shows a user interface 450 for tagging regions of a scanned image, according to an exemplary embodiment of the present subject disclosure. User interface 450 may be depicted on a display of a computer 420, and may be an application such as one of the modules described in FIG. 1, and executed by a processor coupled to computer 420. Interface 450 shows an image 451 of a slide holding a sample. The sample may, for example, take the form of a tissue section obtained from a human or animal subject, such as a formalin-fixed, paraffin-embedded tissue sample. The sample may be living cellular tissue, frozen cells, tumor cells, blood, throat culture, or other; the type or nature of sample is not particularly important. The sample image 451 depicted in FIG. 4 includes a structure imposed upon a background. Interface 450 may be manipulated by an input device, such as a mouse or a keyboard. As shown, the mouse has selected a region 457, and in response, a presentation of options 459 is depicted. Options 459 show a plurality of actions that may be performed by interface 450, such as extracting signals from the selected region, setting the selected region as a reference, applying an existing reference to the selected region, tagging the region for unmixing, or tagging the region to be ignored during unmixing.

For instance, the present example embodiment shows regions 453 and 455 as being tagged respectively as REF1 and REF2. This means that a user, or the software itself, has recognized regions 453 and 455 as containing predominantly broadband signals. This tagging may have been performed subsequent to a command to extract signals from these regions, and a correlation of these signals with known signatures for this type of sample. For instance, image 451 may be that of a tissue section, with region 453 being a portion of the tissue that is predominantly autofluorescent, and region 455 predominantly being a broadband artifact. Further, a region of interest may be the region in between regions 455 and the background, and is selected by the user as region 457. The user now has the option of extracting signals from region 457, which could include unmixing the component signals of this region based on a reference signal. The user may have set a reference signal based on the broadband signals from regions REF2 455 and REF1 453. The user may apply one or more of REF1 and REF2 to an unmixing process on region 457, so as to eliminate noisy broadband signals and extract target signals. The user may further simply tag region 457 as one to be unmixed, and continue tagging, extracting, or setting reference spectra based on additional regions within image 451. Other options may be provided in user interface 450 and may be apparent to persons having ordinary skill in the art upon reading this disclosure.

Figure 5:
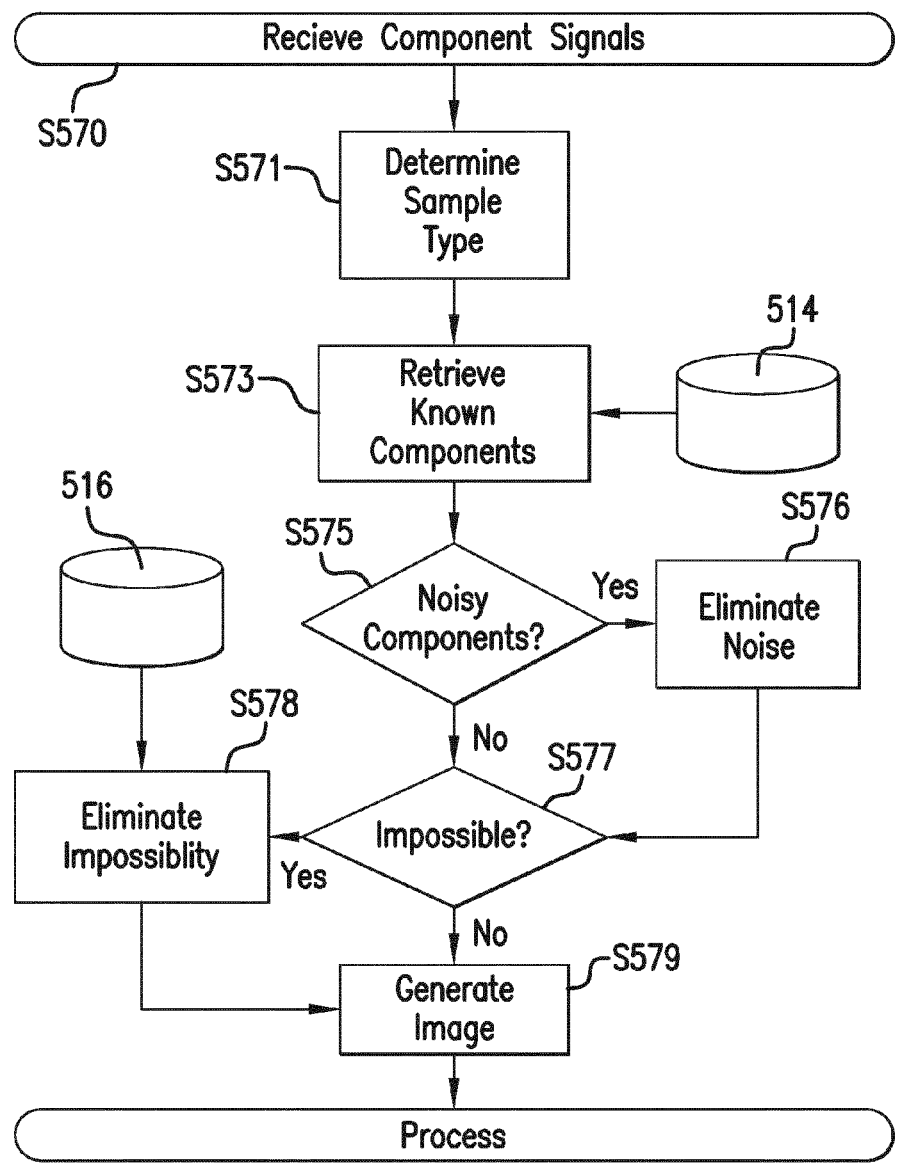
FIG. 5 shows a method for refining desired signals, according to an exemplary embodiment of the present subject disclosure.

FIG. 5 shows a method for refining desired signals, according to an exemplary embodiment of the present subject disclosure. The method of FIG. 5 may be performed by a processor executing modules such as those depicted in FIG. 1. The method begins upon receipt of a plurality of component signals that are derived from a spectral unmixing of an image or a region of an image using a reference spectra matrix to enable extraction of one or more desired signals (S570). Subsequently, a sample type is determined (S571). This may occur by reviewing a tag or metadata associated with the image, input by a user, etc. The type of sample enables a database lookup to retrieve known target component signals for, as an example, the particular sample type (S573). The known target signals may based on something other than the particular sample type. For instance, the target signal depends on the frequency bands being considered and also on the tissue. For the same tissue sample, a very few number of filter bands in one configuration and a very large number of filter bands in another other configuration may result in some minor or subtle changes between the two spectra obtained through the two configurations.

For the same spectral configuration, i.e. the same set of filter bands, the tissue being imaged can cause the spectral signatures to slightly vary. As explained before, the known broadband spectra can vary slightly when acquired from different types of tissue.

A database 514 may store one or more known sets of desired or target signals that correspond to, for example, the type of sample being analyzed. The retrieved sets of known components may be compared with the measured component signals to determine whether any noise or impossible spectra exist (S575-S577). For instance, a system for anatomical or clinical pathology may compare measured quantum dots in an image of a tissue sample with known quantum dot sets to determine if any noisy components, or co-incidence of quantum dots that are unable to co-exist in that tissue sample exist. If any noise is found, the method eliminates known or obvious sources of noise by removing the offending component signal (S576). Further, it is determined using the known components retrieved from database 514 whether or not any impossibility exists (S577). For instance, it may be known that two specific markers, for example, quantum dots are unable to coexist in a certain sample material. Also, a common problem is autofluorescence often being found on the boundary of cells (stained with DAPI) and when it is known that such an occurrence is purely an unmixing artifact, the offending component (autofluorescence in this case) can be removed. Also quantum dots generally occur on the cell nucleus, which contain DAPI stains. Hence, if a low magnitude (when the contribution of the fluorophore $a_{ij}$ is high, we call it a higher magnitude contribution) quantum dot is found in isolation (no DAPI), then it may be an erroneous quantum dot detection and the error can be rectified by discarding the quantum dot. Also, it may be that 2 quantum dots, say quantum dot A and quantum dot B, are not known to co-exist. In such a case, when we have a low magnitude detection of quantum dot A with a high magnitude detection of quantum dot B, then it is likely that the detection of quantum dot A is an artifact of unmixing and the noisy component (quantum dot A) is eliminated. A quantum dot amplitude may be X times stronger than another fluorophore in order to ignore the effect of that fluorophore. For example, if X=20, and the quantum dot strength is 300 units of measured spectral magnitude (i.e. in the terms of the pixel intensity of the hyperspectral image), then if any fluorophore, after unmixing, is found to have a value less than (300/20=15), then the effect of that fluorophore may be ignored.

These and other impossibilities may be recognized and accounted for by removing the offending signal, leaving behind a refined set of desired signals (S578). The known impossibility may be retrieved from database 516, 514, or any other data store in communication with the system, or a skilled operator of the system, such as a pathologist or knowledgeable technician. In other words, what is known about the type of sample under analysis may be provided by a database or by an operator of the system, with such a priori knowledge being useful in eliminating noise, refining results, and generating a clean image suitable for subsequent analysis or diagnosis.

Figure 6A:
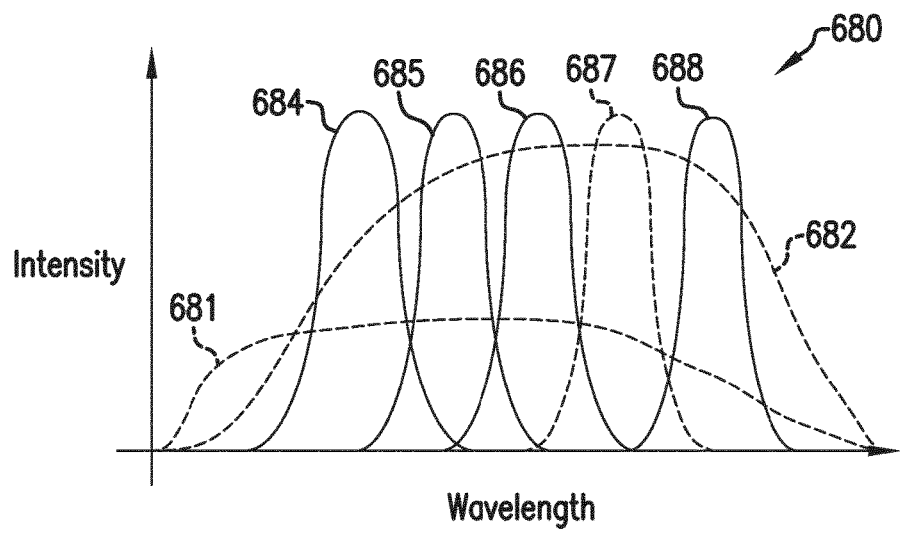
FIGS. 6A and 6B show before and after images of a detected emission spectra, according to an exemplary embodiment of the present subject disclosure.
Figure 6B:
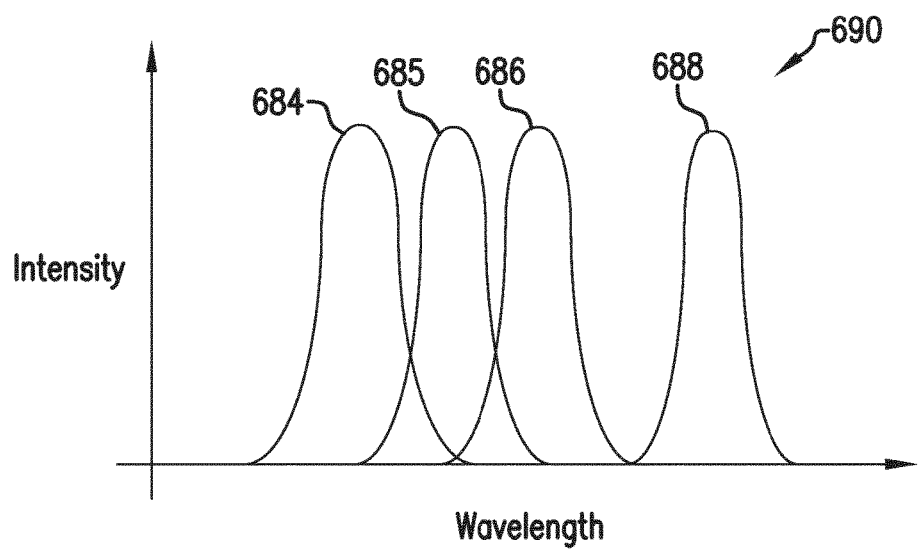

FIGS. 6A and 6B show before and after images of a detected emission spectra, according to an exemplary embodiment of the present subject disclosure. FIG. 6A shows a graph 680 depicting a plurality of component signals that have been unmixed by a spectral unmixing or other process. The plurality of component signals includes broadband signals 681 and 682, as well as quantum dot signals 684, 685, 686, 687, and 688. Subsequent to broadband removal and post-processing, FIG. 6B shows a graph 690 depicting only the refined target signals that may be used to generate an image for diagnosis or analysis. For instance, depending on the sample type, it may be known that quantum dots 684 and 687 are unable to co-exist, whereas quantum dots 684, 685, 686 and 688 are all able to co-exist for the particular sample type. Therefore, a post-processing refinement method as shown in FIG. 5 would indicate such impossibility, and would remove the offending signal 687 from the refined set of signals. Consequently, known information about a particular sample may enable clearer image generation and more accurate analysis.

Figure 7:
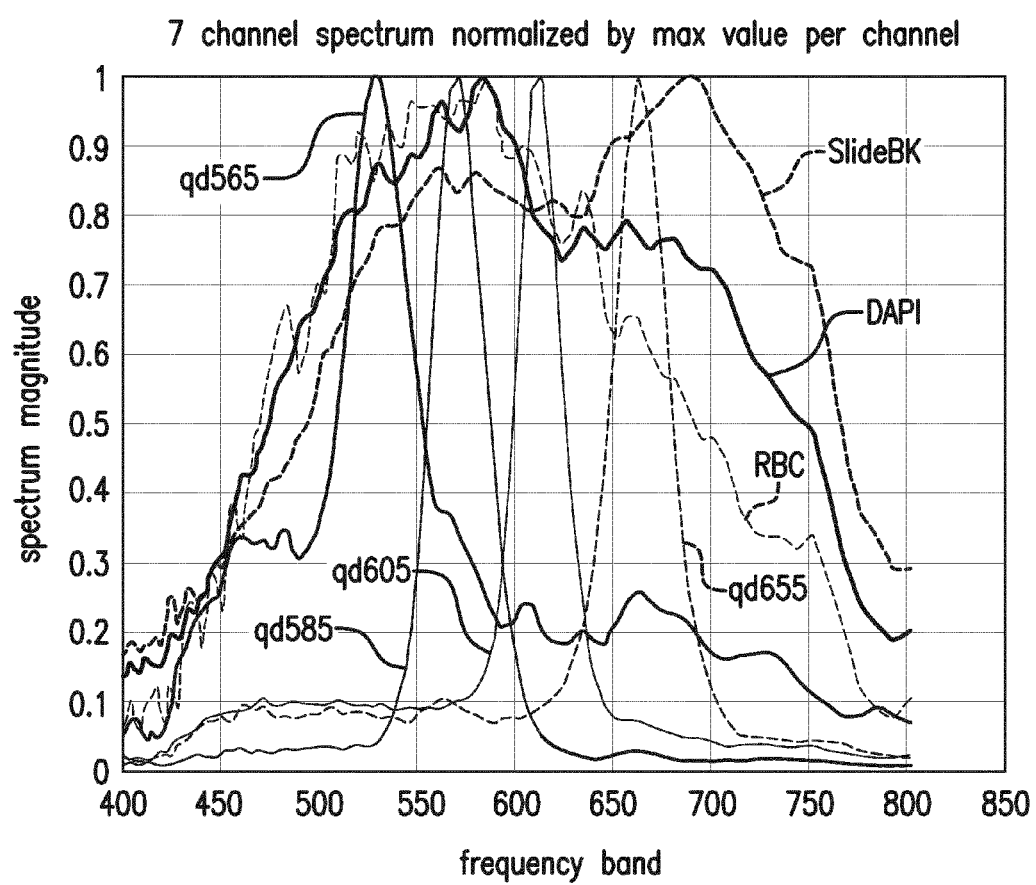
FIG. 7 shows a plurality of normalized reference spectra, according to an exemplary embodiment of the subject disclosure.
Figure 8A:
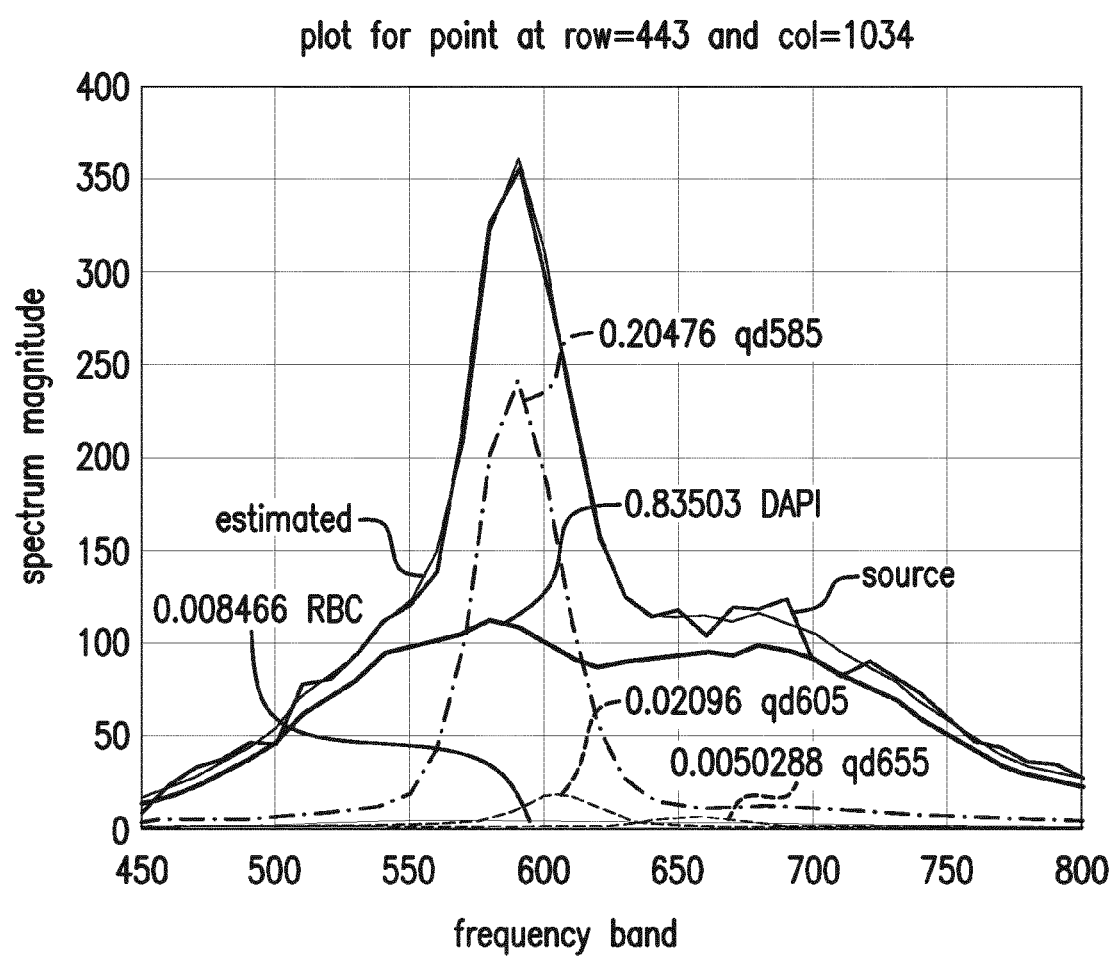
FIGS. 8A-8D show a plurality of estimated spectra shown as a result of unmixing, according to exemplary embodiments of the subject disclosure.
Figure 8B:
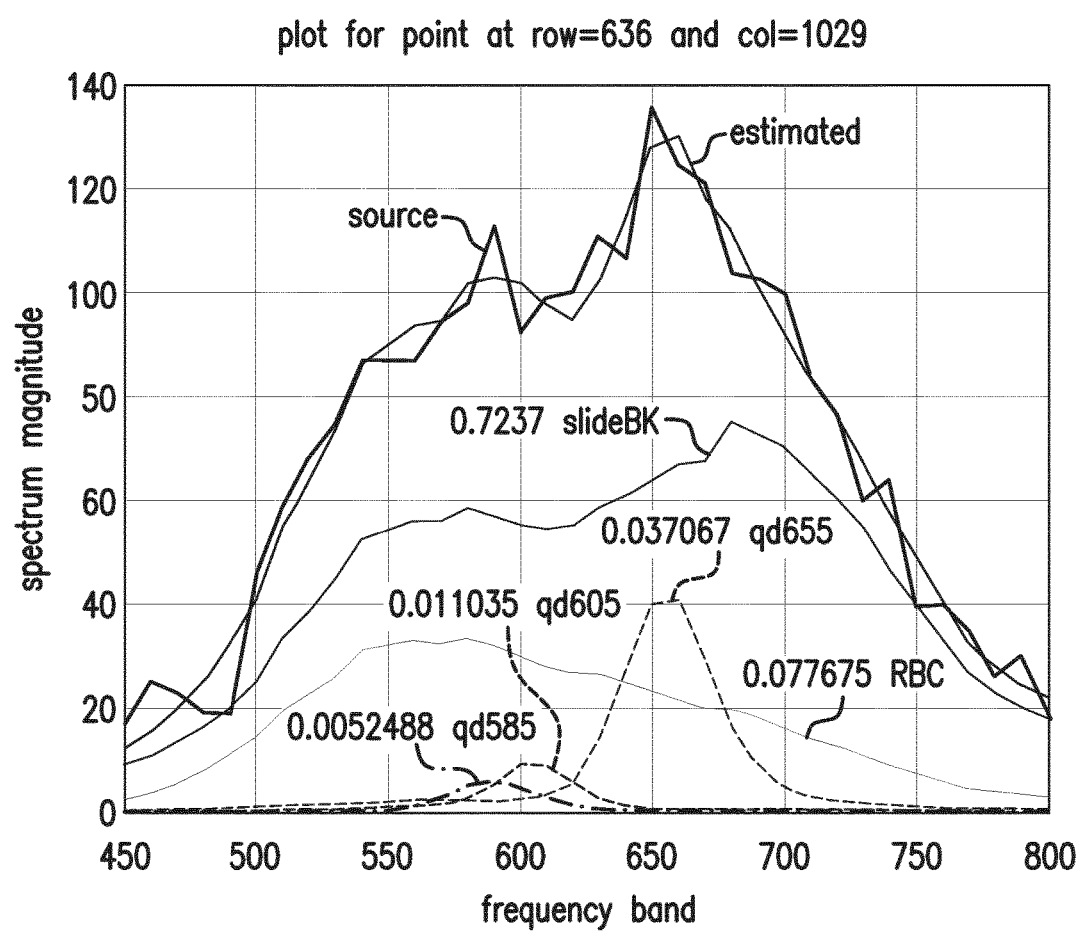
Figure 8C:
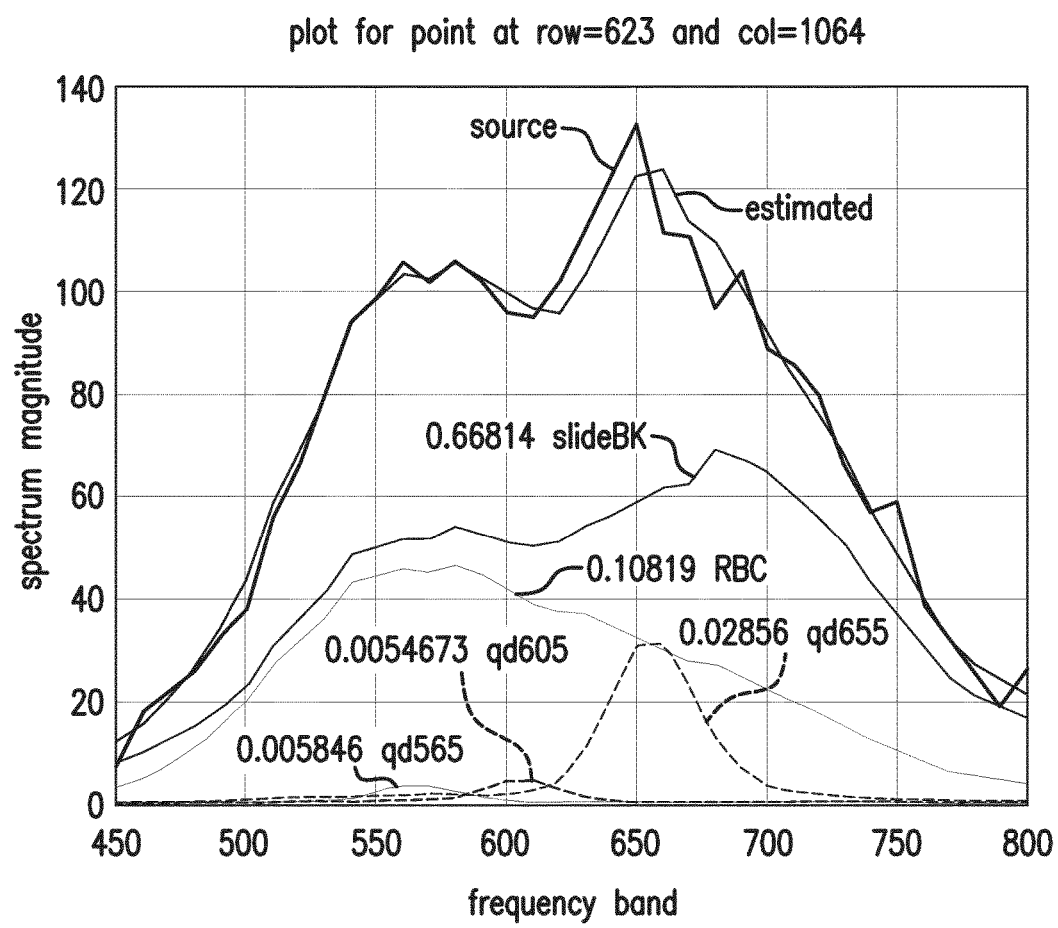
Figure 8D:
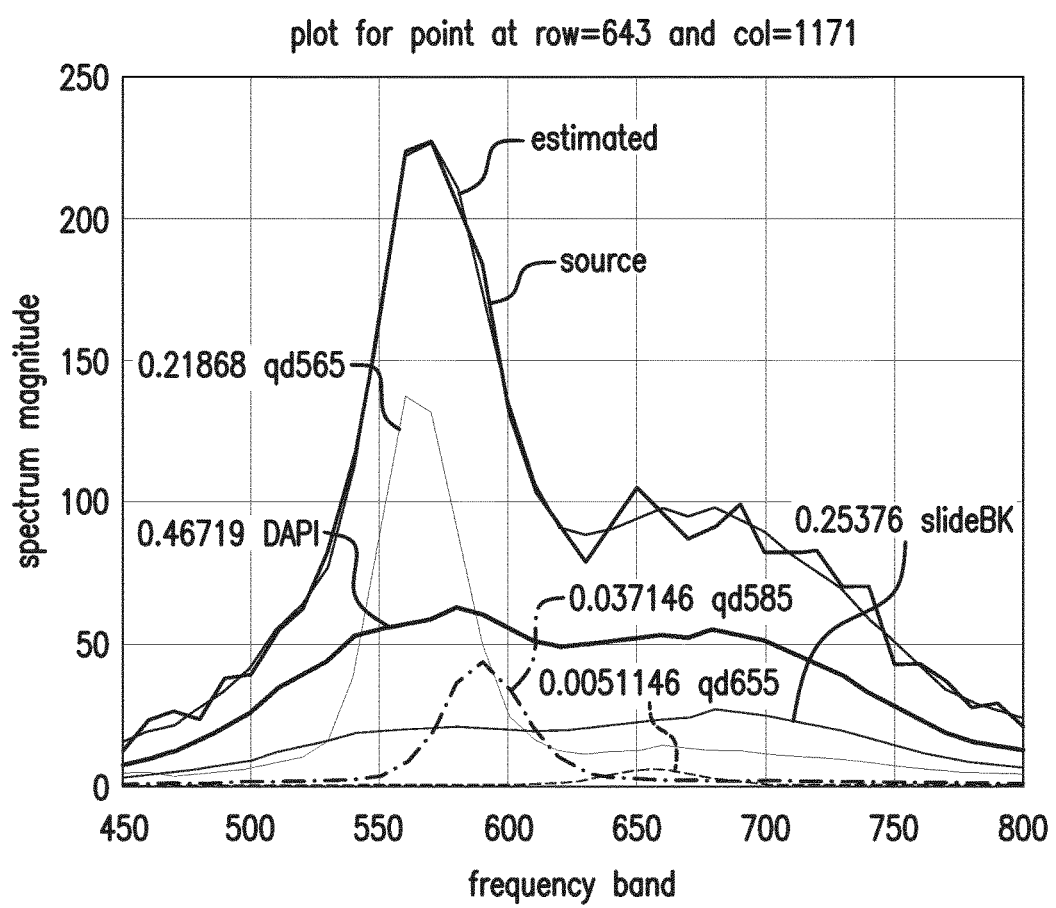

FIG. 7 shows a plurality of normalized reference spectra, according to an exemplary embodiment of the subject disclosure. Normalized reference spectra are shown for the frequency bands from 400-800 nm, with different fluorophores including quantum dot 565 (qd565), quantum dot 585 (qd585), quantum dot 605 (qd605), quantum dot 655 (qd655), DAPI, RBC (red blood cells) and slide background (SlideBK), as identified in key 791. According to this embodiment, the quantum dot spectra are very narrow-band spectra; e.g. qd655 is a very narrowband spectrum and while it peaks at 655 nm, its bandwidth (when it falls to less than 10% of peak value) is less than 100 nm. It is seen that while the quantum dots spectra are narrowband, the DAPI, RBC and SlideBK have wideband spectral signatures. Also, the fact that many fluorophores, which participate in the mixing process, have wideband spectra lead to problems in linear unmixing; i.e. in accurately recovering the weight terms involved in the mixing process. The presence of spectral signatures where each signature is more different from the other leads to better discriminability among reference signatures and also makes the unmixing more accurate.

FIGS. 8A-8D show a plurality of estimated spectra shown as a result of unmixing, according to exemplary embodiments of the subject disclosure. In each case, an observed spectrum is plotted, spectral unmixing is performed in accordance with the methods disclosed herein, spectral signatures for each fluorophore are plotted and weighted by a weighting term obtained through the spectral unmixing; and an estimated spectrum is plotted, which is obtained as a linear combination of the reference spectra of the fluorophores, where the weighting terms obtained after spectral unmixing are used. The closeness between the source and estimated spectra shows the effectiveness of the unmixing process described herein.

The disclosed systems and methods therefore enable generation of an image substantially consisting of desired or precise signals without any broadband noise or undesired fluorescent artifacts. For instance, autofluorescence, DAPI, and other undesired signatures may be subtracted from a scanned image of a tissue sample, leaving behind only biologically relevant information. Moreover, once predominantly broadband or noisy regions are determined for a particular slide or set of slides, these regions need not be unmixed, resulting in a less intensive unmixing process. The disclosed features therefore enable efficient image analysis, identification of structures, accurate diagnoses, etc. Broadband signals from artifacts such as RBCs, autofluorescence from lipofuscin, etc. can no longer mask or overpower desired fluorophore signals such as quantum dots, etc. Besides medical applications such as anatomical or clinical pathology, prostrate/lung cancer diagnosis, etc., the same methods may be performed to analysis other types of samples such as remote sensing of geologic or astronomical data, etc. Further, the disclosed methods may be repeatedly iterated to refine the results. For large or multiple slide/image analysis, or for analyzing one or more image cubes, the operations described herein may be ported into a hardware graphics processing unit (GPU), enabling a multi-threaded parallel implementation.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A non-transitory computer-readable medium for storing computer-executable instructions that are executed by a processor to perform operations comprising: receiving an image comprising a mixture of signals, the mixture of signals further comprising a measured broadband signal and a target signal;
   detecting a location of a first region of the image, the first region predominantly comprising the measured broadband signal, the detecting being based on a comparison of the measured broadband signal with a known broadband signal;
   estimating a reference signal for the image based on the measured broadband signal; and
   utilizing the reference signal to spectrally unmix the mixture, wherein the first region is excluded from said spectral unmixing.

2. The computer-readable medium of claim 1, wherein the known broadband signal is retrieved from a calibration image.

3. The computer-readable medium of claim 1, wherein the comparison comprises comparing a signature of the measured broadband signal with a signature of the known broadband signal.

4. The computer-readable medium of claim 3, wherein the signature of the measured broadband signal is determined by sampling a plurality of pixels of the image, extracting a pixel signature from each pixel, and averaging the extracted pixel signatures to determine the signature of the measured broadband signal.

5. The computer-readable medium of claim 4, wherein detecting the location of the first region further comprises comparing the signature of the measured broadband signal to a plurality of regions within the image.

6. The computer-readable medium of claim 1, wherein the tagging is performed via a user interface.

7. The computer-readable medium of claim 1, further comprising generating a matrix comprising the reference signal, wherein the matrix is used to spectrally unmix the mixture.

8. The computer-readable medium of claim 7, wherein the matrix further comprises a narrowband signal corresponding to the target signal.

9. The computer-readable medium of claim 1, wherein the measured broadband signal comprises one or more of a 4',6-diamidino-2-phenylindole (DAPI) signal, and an autofluorescence signal.

10. The computer-readable medium of claim 1, wherein the target signal is one among a plurality of target signals, and wherein the operations further comprise refining the plurality of target signals to extract a refined set of target signals.

11. The computer-readable medium of claim 10, wherein the refining further comprises eliminating one or more of a known noise and an impossibility from the plurality of target signals.

12. The computer-readable medium of claim 10, further comprising generating a second image from the refined set of target signals.

13. A non-transitory computer-readable medium for storing computer-executable instructions that are executed by a processor to perform operations comprising: detecting a predominantly broadband region of an image, the image comprising a mixture of broadband signals and target signals; estimating a reference signal from the predominantly broadband region; and unmixing the mixture using the reference signal to extract the target signal, wherein the predominantly broadband region is exempt from said unmixing.

14. The computer-readable medium of claim 13, wherein the operations further comprise comparing a signature of the predominantly broadband region with a signature of a known broadband signal.

15. The computer-readable medium of claim 13, wherein the operations further comprise receiving a selection of a target region of the image for unmixing.

16. The computer-readable medium of claim 13, wherein the reference signal is part of a matrix.

17. The computer-readable medium of claim 16, wherein the matrix is used to unmix the mixture.

18. A system for diagnosis of a tissue specimen, the system comprising:
a computer including a processor and a memory;
a reference spectra determination module on the memory for detecting a location of a first region of an image, the image comprising a mixture of a measured broadband signal and a target signal, the first region predominantly comprising the measured broadband signal, the detecting being based on a comparison of the measured broadband signal with a known broadband signal, and estimating a reference signal for the image based on the measured broadband signal; and
an unmixing module on the memory for unmixing the mixture using a matrix comprising the reference signal as input in order to derive the target signal, wherein the first region is excluded from said unmixing.

19. Method for spectral unmixing, the method comprising:
scanning a slide holding a sample of a stained material using a fluorescent microscope to generate a scanned image, wherein the material is stained by means of application of a stain containing one or more different fluorophores, and wherein the scanned image comprises a mixture of signals, the mixture of signals further comprising a measured broadband signal and a target signal;
detecting a location of a first region of the image, the first region predominantly comprising the measured broadband signal, the detecting being based on a comparison of the measured broadband signal with a known broadband signal;
estimating a reference signal for the image based on the measured broadband signal; and
utilizing the reference signal to spectrally unmix the mixture, wherein the first region is excluded from said spectral unmixing.

20. The method of claim 19, wherein the known broadband signal is retrieved from a calibration image.

21. The method of claim 19, wherein the comparison comprises comparing a signature of the measured broadband signal with a signature of the known broadband signal.

22. The method of claim 21, wherein the signature of the measured broadband signal is determined by sampling a plurality of pixels of the image, extracting a pixel signature from each pixel, and averaging the extracted pixel signatures to determine the signature of the measured broadband signal.

23. The method of claim 22, wherein detecting the location of the first region further comprises comparing the signature of the measured broadband signal to a plurality of regions within the image.

24. The method of claim 19, wherein the tagging is performed via a user interface.

25. The method of claim 19, further comprising generating a matrix comprising the reference signal, wherein the matrix is used to spectrally unmix the mixture.

26. The method of claim 25, wherein the matrix further comprises a narrowband signal corresponding to the target signal.

27. The method of claim 19, wherein the measured broadband signal comprises one or more of a 4',6-diamidino-2-phenylindole (DAPI) signal, and an autofluorescence signal.

28. The method of claim 19, wherein the target signal is one among a plurality of target signals, and wherein the method further comprises refining the plurality of target signals to extract a refined set of target signals.

29. The method claim 28, wherein the refining further comprises eliminating one or more of a known noise and an impossibility from the plurality of target signals.

30. The method of claim 28, further comprising generating a second image from the refined set of target signals.

* * * * *